(12) United States Patent
Hofbauer et al.

(10) Patent No.: US 11,786,412 B2
(45) Date of Patent: Oct. 17, 2023

(54) DERMAL PATCH

(71) Applicant: Carl Freudenberg KG, Weinheim (DE)

(72) Inventors: Thomas Hofbauer, Hirschberg (DE); Daniela Beyer, Weinheim (DE); Sandra Villing-Falusi, Mannheim (DE)

(73) Assignee: CARL FREUDENBERG KG, Weinheim (DE)

( * ) Notice: Subject to any disclaimer, the term of this patent is extended or adjusted under 35 U.S.C. 154(b) by 389 days.

(21) Appl. No.: 16/307,152

(22) PCT Filed: Jun. 8, 2017

(86) PCT No.: PCT/EP2017/064009
§ 371 (c)(1),
(2) Date: Dec. 5, 2018

(87) PCT Pub. No.: WO2018/007093
PCT Pub. Date: Jan. 11, 2018

(65) Prior Publication Data
US 2019/0133829 A1     May 9, 2019

(30) Foreign Application Priority Data

Jul. 8, 2016 (DE) ..................... 10 2016 008 257.7

(51) Int. Cl.
*A61F 13/02* (2006.01)
*A61L 15/42* (2006.01)
(Continued)

(52) U.S. Cl.
CPC ...... *A61F 13/0206* (2013.01); *A61F 13/0203* (2013.01); *A61F 13/0253* (2013.01);
(Continued)

(58) Field of Classification Search
CPC ............... A61F 13/00; A61F 13/00008; A61F 13/00085; A61F 13/0246; A61F 13/0206;
(Continued)

(56) References Cited

U.S. PATENT DOCUMENTS 3,972,328 A   8/1976 Chen
3,975,567 A   8/1976 Lock
(Continued)

FOREIGN PATENT DOCUMENTS

AT   332564 B   10/1976
DE   2631277 A1   2/1977
(Continued)

OTHER PUBLICATIONS

Anonymous: "Medisponge SuperSoft™ Foams", Dec. 3, 2015 (Dec. 3, 2015), XP055388697.

*Primary Examiner* — Caitlin A Carreiro
(74) *Attorney, Agent, or Firm* — LEYDIG, VOIT & MAYER LTD.

(57) ABSTRACT

A dermal patch includes: an open-cell foam layer; and an adhesive layer arranged thereon and intended for contact with skin. At least a side of the foam layer facing the adhesive layer has macropores whose cavities are spanned at least partially by a barrier layer formed from the foam layer.

18 Claims, 8 Drawing Sheets

(51) Int. Cl.
 *A61L 15/26* (2006.01)
 *A61L 15/58* (2006.01)
 *A61F 13/00* (2006.01)

(52) U.S. Cl.
 CPC .......... *A61F 13/0289* (2013.01); *A61L 15/26* (2013.01); *A61L 15/425* (2013.01); *A61L 15/58* (2013.01); *A61F 2013/0074* (2013.01); *A61F 2013/00782* (2013.01)

(58) Field of Classification Search
 CPC .............. A61F 13/0203; A61F 13/0253; A61F 13/0289; A61F 2013/0074; A61F 2013/00782; A61F 2013/00634; A61F 2013/0251; A61F 2013/00255; A61F 5/443; A61L 15/26; A61L 15/425; A61L 15/58; A61L 31/146; A61K 9/7038; A61K 9/7084; A61K 9/7092
 USPC ................. 602/1–43, 46, 47, 52, 54, 56, 58; 424/445, 448, 449; 604/304, 307; 428/391; 128/888–890
 See application file for complete search history.

(56) References Cited

U.S. PATENT DOCUMENTS

| | | | |
|---|---|---|---|
| 3,978,855 A * | 9/1976 | McRae | A61L 15/48 521/905 |
| 4,538,603 A | 9/1985 | Pawelchak et al. | |
| 4,728,642 A * | 3/1988 | Pawelchak | A61L 26/008 514/59 |
| 4,921,704 A | 5/1990 | Fabo | |
| 5,643,234 A * | 7/1997 | Lesko | A61F 5/441 604/338 |
| 6,306,424 B1 * | 10/2001 | Vyakarnam | A61L 31/146 428/338 |
| 8,242,325 B2 | 8/2012 | Leumann et al. | |
| 2002/0094742 A1 * | 7/2002 | Jones | D04H 1/60 442/394 |
| 2004/0018227 A1 * | 1/2004 | Park | A61F 13/00991 424/445 |
| 2004/0138605 A1 | 7/2004 | Sigurjonsson et al. | |
| 2005/0169975 A1 * | 8/2005 | Suzuki | A61L 15/26 424/448 |
| 2010/0222730 A1 | 9/2010 | Leumann et al. | |
| 2011/0112458 A1 * | 5/2011 | Holm | A61L 15/58 602/54 |
| 2011/0117178 A1 * | 5/2011 | Junginger | A61P 17/02 424/445 |
| 2012/0244350 A1 * | 9/2012 | Cimpeanu | C09J 133/12 156/332 |

FOREIGN PATENT DOCUMENTS

| | | |
|---|---|---|
| EP | 0251810 A2 | 1/1988 |
| EP | 0300620 A1 | 1/1989 |
| EP | 0855921 B1 | 1/2002 |
| EP | 1820520 A1 | 8/2007 |
| EP | 1964580 B1 | 12/2010 |
| EP | 2001424 B1 | 11/2011 |
| EP | 2696824 B1 | 3/2015 |
| EP | 1981550 B1 | 7/2016 |

* cited by examiner

DERMAL PATCH

CROSS-REFERENCE TO PRIOR APPLICATIONS

This application is a U.S. National Phase application under 35 U.S.C. § 371 of International Application No. PCT/EP2017/064009, filed on Jun. 8, 2017, and claims benefit to German Patent Application No. DE 10 2016 008 257.7, filed on Jul. 8, 2016. The International Application was published in German on Jan. 1, 2018 as WO 2018/007093 under PCT Article 21(2).

FIELD

The invention relates to a dermal patch, in particular a wound dressing, comprising a substrate layer and an adhesive layer arranged thereon, as well as a method for its production.

BACKGROUND

Cosmetic and medical dermal patches for use on humans have long been known.

A particularly important group of dermal patches is used in wound care.

In modern wound care, wound dressings that have a substrate layer and an adhesive layer arranged thereon are frequently used. Polyurethane foams in particular have proven to be useful as the substrate layer since they have good climate-regulating and absorbing properties, and can be placed in direct contact with the exuding wound. In addition, polyurethane foams used for wound care generally have an open cell structure, giving them a high absorbency and allowing for rapid absorption of the wound exudate.

For the last two decades, substrate layers have often additionally been provided on the wound side with an adhesive layer which adheres to healthy skin but not in contact with the wound. In contact with the wound, this adhesive layer, which in most cases is silicone-based, even has the advantage that it prevents adherence or ingrowth of the newly formed tissue in the case of moist wounds, does not cause any pain during removal of the dressing, and prevents the wound from tearing open again.

A disadvantage of the use of conventional silicone-based adhesive layers is that they make absorption of the wound exudate difficult because of their hydrophobic properties and their low water vapor permeability. In order to compensate for this, the silicone adhesive layer generally has perforations. This is intended to make it possible for the accumulating exudate to pass through the adhesive layer into the absorbent foam, and thus an ideally moist wound climate can adjust. Despite the perforations, the silicone adhesive layer is cohesive. This has the disadvantage that, when wound exudate is absorbed, free swelling of the foam layer is prevented by the silicone adhesive layer. As a result, the dermal patch bulges away from the wound, whereby absorption of further wound exudate is made more difficult thereafter.

The transfer coating method has become established for applying the adhesive layer. In doing so, a film, for example a polyurethane film, is initially coated by means of knife coating and roller coating with an acrylate adhesive on one side and with a soft silicone adhesive on the other side. The silicone adhesive precursor compositions used in the process consist of two components which, after mixing, thermally crosslink to form a soft, gel-like solid. The sandwich of acrylate adhesive/film/silicone adhesive produced in the transfer coating method is then perforated and subsequently adhered to the substrate with the acrylate adhesive side.

Such a transfer coating method is, for example, described in EP 2001424 B1. In this case, a wound dressing is produced which comprises a skin contact layer in the form of a releasable adhesive laminate comprising a structural layer that carries a hydrophobic gel on at least a portion of one side thereof, and a pressure-sensitive adhesive on at least a portion of the other side thereof. The structural layer preferably consists of a plastic film. The disadvantage of using this plastic film is that it has a high degree of rigidity and low adaptability. Consequently, a comparatively high amount of silicone must be used for compensation, which results in higher costs. A large layer thickness also requires a comparatively high amount of energy for curing the precursor compounds. In addition, the use of a film and a high amount of silicone degrades the water vapor permeability of the wound dressing.

EP 0855921 B1 describes a foam wound dressing and its production. In this case, a film is coated with a silicone adhesive, and then a polyurethane foam is placed directly on the yet uncured silicone. By curing the silicone in a furnace, this laminate is then bonded. An open-cell absorbent foam with pore sizes between 30 and 1,000 µm is used as the foam material. The disadvantage of the described polyurethane foam structure is that, because the gel is absorbed by the foam, the absorbed portion of the gel is no longer available for adhesion to the skin.

US 2004/0138605 A1 describes wound dressings with an absorbent core, preferably made of open-cell foam, on which a pressure-sensitive adhesive can be arranged. This pressure-sensitive adhesive is preferably a silicone or acrylate adhesive suitable for wound care. The adhesive layer can be a silicone which is sprayed onto the (wound-side) cover layer of the wound dressing.

Because of the open-cell surface, a comparatively high amount of silicone is also required in this case.

EP 2696824 B1 describes a discontinuous application of a silicone adhesive in a modified screen printing or apertured roller process. Polyurethane foams and nonwovens are mentioned as substrates, among other things. In this process, a regular pattern of discrete, small adhesive surfaces, such as a dot pattern, is produced from silicone adhesive. The layer thickness of the silicone adhesive during screen printing is implicitly predetermined by the thickness of the screen. This thickness is 100-2,000 µm, so that the layer thickness is also comparatively large in this case.

EP 1964580 B1 describes a method for producing a hydrophilic polyurethane foam structure containing a silver salt. In this case, a foam-forming polyurethane dispersion is provided and applied to a casting paper. The polyurethane foam is then cured, the casting paper is removed, and the foam is dried. A silicone gel is applied to the surface of the open-cell foam structure formed in this way and cured. In doing so, a larger portion of the gel is absorbed by the foam.

The disadvantage of the described polyurethane foam structure is that, because the gel is absorbed by the foam, the absorbed portion of the gel is no longer available for adhesion to the skin.

SUMMARY

In an embodiment, the present invention provides a dermal patch, comprising: an open-cell foam layer; and an adhesive layer arranged thereon and configured for contact with skin, wherein at least a side of the foam layer facing the adhesive layer has macropores whose cavities are spanned at least partially by a barrier layer formed from the foam layer.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
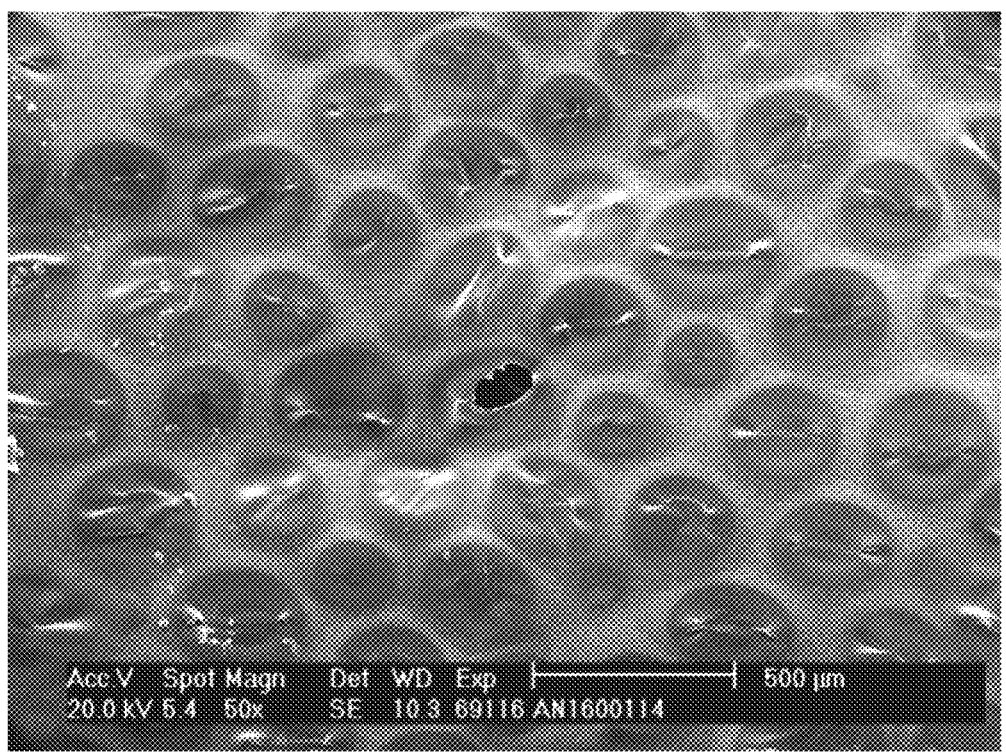
FIG. 1 SEM image of a foam layer in a plan view (according to the invention)

As explained above, the application of a high amount of silicone makes the products significantly more expensive. That is why the object of the invention is to provide a dermal patch of the aforementioned type which makes it possible to keep the thickness of the adhesive layer small and achieve high performance, in particular good absorbency for wound exudate. The dermal patch is also to be slip-resistant, easy to remove, and repositionable.

This object is achieved by a dermal patch, in particular a wound dressing, comprising an open-cell foam layer and an adhesive layer arranged thereon and intended for contact with the skin, wherein at least the side of the foam layer facing the adhesive layer has macropores whose cavities are spanned at least partially by a barrier layer formed from the foam layer.

According to the invention, it has been found that, by using a foam layer which has a barrier layer formed from the foam layer at least on the side facing the adhesive layer, it is possible to use only a small amount of adhesive and nevertheless achieve good adhesion. The presence of the barrier layer is believed to at least partially prevent penetration of the adhesive into the foam layer. Less adhesive is thereby required in order to achieve a locally closed coating. This is a great advantage in comparison to the foams which are used in the prior art, are open-celled at the surface, and for which a large amount of adhesive must be used. In addition, the provision of a barrier layer formed from the foam layer has the advantage that no further layers, for example separate films, which prevent the penetration of adhesive, have to be produced, applied, and adhesively bonded in a costly manner.

In addition, the dermal patch when used as a wound dressing has the advantage, even in comparison to foams that are open-celled at the surface, that the barrier layer can prevent ingrowth of newly forming tissue. In this way, damage to the newly formed tissue can be avoided when changing the wound dressing.

Furthermore, it has surprisingly been found that, despite the existing barrier layer, the foam layer can exhibit very good absorbency for wound exudate, sweat, and water vapor. Thus, the dermal patch advantageously has an absorbency of at least 5 g/g, for example from 5 g/g to 50 g/g, preferably from 10 g/g to 30 g/g, and more preferably from 15 g/g to 25 g/g. The barrier layer is also preferably designed such that the dermal patch also has a very good absorption time, which naturally depends on the type, amount, and degree of coverage of the adhesive layer.

According to the invention, at least the side of the foam layer facing the adhesive layer has macropores which preferably adjoin the surface and whose cavities are spanned at least partially by a barrier layer formed from the foam layer. This embodiment makes it possible to design the barrier layer planar, whereby the amount of adhesive can be kept even smaller. According to the invention, the term "planar" is understood in the conventional sense. The barrier layer preferably has a planarity, measured as described in the Section "Measuring methods," of less than 50 μm, for example from 0.1 μm to 50 μm, preferably from 1 μm to 30 μm, more preferably from 1 μm to 20 μm, and in particular from 1 μm to 10 μm. According to the invention, the term "planarity" may include smaller irregularities of the barrier layer, for example smaller waves and/or folds.

"Macropores" are understood according to the invention to mean pores which have a pore diameter of more than 25 μm, for example between 25 μm and 2,000 μm, and preferably between 100 μm and 500 μm.

According to the invention, the foam layer has a barrier layer at least on the side facing the adhesive layer so that the macropores adjoining the surface can be considered at least partially to be closed-celled at least in the direction toward the adhesive layer. Nevertheless, the foam layer is open-celled in volume, which means that the cell walls inside the foam are at least partially destroyed. In comparison to a foam which is also closed-celled in volume, the higher absorbency for wound exudate is advantageous, for example with respect to use in a wound dressing. For this purpose, the foam layer is advantageously so open-celled that the foam layer has an absorbency of at least 5 g/g, for example from 5 g/g to 50 g/g, preferably from 10 g/g to 30 g/g, and more preferably from 15 g/g to 25 g/g.

According to the invention, the barrier layer is formed from the foam layer so that the barrier layer can be regarded as part of the foam layer and can at least in some regions constitute the surface of the foam layer.

The barrier layer and the foam layer are generally present as a uniform material, wherein production-related enrichments of individual components are to be considered encompassed by the term "uniform material."

According to the invention, both sides or only one side of the foam layer may have a barrier layer formed from the foam layer. If one side of the foam layer has a larger percent area of the barrier layer, this side preferably forms the side facing the adhesive layer.

The barrier layer is expediently formed during the production of the foam layer. This can be done in a simple manner by foaming a suitable foam mixture freely in air. In doing so, a skin, which constitutes the barrier layer, can develop on the surface of the foam. The formation of the barrier layer can alternatively also take place by applying the foam mixture to a support material, for example a casting paper. Without determining a mechanism, it is believed that, upon contact with the casting paper, the macropores arranged on the surface facing the casting paper are formed and spanned by the barrier layer. It has been found in practical experiments that a high proportion of spanned macropores can be achieved by using hydrophobic casting papers.

The barrier layer may have micropores, i.e., pores having a pore diameter of 25 µm or less, for example from 0.01 µm to 25 µm. The micropores are advantageous in that they can lend the dermal patch an improved permeability for wound exudate, sweat, and water vapor. For this purpose, the micropores are preferably designed open-celled.

According to the invention, preferably at least 20%, for example 20% to 100%, preferably 70% to 100%, more preferably 90% to 100%, even more preferably 95% to 100%, and in particular 98% to 100% of the macropores adjoining the surface of the foam layer are spanned by the barrier layer.

In a further preferred embodiment, the percent area of the barrier layer to the surface of the foam layer is at least 20%, for example 20% to 100%, preferably 70% to 100%, and in particular 95% to 100%.

According to the invention, the barrier layer is preferably thin. Its thickness is preferably less than 100 µm, for example from 0.01 µm to 100 µm, more preferably from 0.1 µm to 50 µm, even more preferably from 0.3 µm to 20 µm, yet even more preferably from 0.4 µm to 10 µm, and in particular from 0.5 µm to 3 µm. In a preferred embodiment, the barrier layer is so thin that, in a plan view in an optical evaluation of SEM images, the macropores can still be seen under the barrier layer with a magnification of, for example, 30, as in FIG. 1, for example. An uncoated foam layer is shown in FIG. 1. If the adhesive layer is sufficiently thin, a coated foam layer can also be examined in the same way. A thin barrier layer is advantageous in that it has a higher permeability for wound exudate, sweat and water vapor and is nevertheless impermeable to adhesives customary in wound care, in particular to silicone adhesives and their precursor compositions.

According to the invention, the cavities of the macropores adjoining the surface of the foam layer are preferably spanned at least partially by the barrier layer. In this respect, the term "spanning" is to be understood to mean a covering of the cavities to form a closed cavity. Functionally, the spanning with the barrier layer is to at least partially prevent penetration of the liquid adhesive or its precursor compositions. In the case of a perforation of the barrier layer, penetration of the adhesive or its precursor compositions can no longer be reliably prevented, at least at this point.

The barrier function of the barrier layer makes it possible to apply the adhesive layer directly to the surface of the foam layer so that penetration of the adhesive into the foam layer can be prevented or at least reduced. In a preferred embodiment of the invention, the adhesive layer is therefore arranged directly on the surface of the foam layer, wherein "directly" is to be understood to mean that no further layers are arranged between the adhesive layer and the foam layer.

In a preferred embodiment of the invention, the adhesive layer has a thickness of less than 300 µm, for example between 1 µm and 300 µm, preferably between 1 µm and 100 µm, more preferably between 1 µm and 90 µm, even more preferably between 1 µm and 50 µm, yet even more preferably between 2 µm and 30 µm, still more preferably between 3 µm and 20 µm, and in particular between 5 µm and 15 µm.

A thin adhesive layer is advantageous in that the water vapor permeability is higher, and any active substances contained in the foam layer may be present at a lesser distance to their site of action in the wound.

In a further preferred embodiment of the invention, the applied quantity of the adhesive layer is less than 200 g/m$^2$, for example from 1 g/m$^2$ to 200 g/m$^2$, preferably from 1 g/m$^2$ to 100 g/m$^2$, more preferably from 1 g/m$^2$ to 90 g/m$^2$, even more preferably from 1 g/m$^2$ to 50 g/m$^2$, yet even more preferably 2 g/m$^2$ to 30 g/m$^2$, still more preferably 3 g/m$^2$ to 20 g/m$^2$, and in particular from 5 g/m$^2$ to 15 g/m$^2$.

The advantage of a small applied quantity of the adhesive layer is the reduction of the costs incurred, in particular the material and energy costs.

It was found in practical tests that the dermal patch according to the invention can exhibit good adhesion even with a low applied quantity of the adhesive layer. The adhesion of the dermal patch to a steel substrate is thus preferably more than 0.05 N/2.5 cm, for example from 0.05 N/2.5 cm to 5 N/2.5 cm, preferably from 0.05 N/2.5 cm to 1 N/2.5 cm, and particularly preferably from 0.05 N/2.5 cm to 0.2 N/2.5 cm even with the aforementioned low applied quantities, i.e. for example with less than 200 g/m$^2$.

The adhesive layer may cover the foam layer partially or completely. According to the invention, the adhesive layer preferably covers the foam layer only partially since this facilitates permeation by wound exudate. In this case, the degree of coverage is preferably less than 99%, for example from 10% to 99%, preferably from 30% to 95%, and in particular from 50% to 90%.

The foam layer may be partially covered in different ways, for example by mask application or by subsequent removal of the adhesive layer in regions. This removal can be carried out in such a way that portions of the underlying foam layer, including the barrier layer, are additionally also removed. At these points, the surface of the foam layer is consequently not formed by the barrier layer.

In this embodiment of the invention, preferably from 10% to 99%, more preferably from 30% to 95%, and in particular from 70% to 90% of the surface of the foam layer is formed by the barrier layer.

Those regions of the foam layer which no longer have a barrier layer are also not covered by the adhesive layer and are formed, for example, as depressions and/or holes. The depressions and/or holes can assume a wide variety of forms of a regular or irregular pattern, for example as a lattice, hole, dot, dash, line, polygon, for example diamond or honeycomb, circle, cross, spot, and/or island pattern. The depressions and/or holes may, for example, be distinguished from the micropores or macropores present in the foam layer in that they were subsequently introduced.

The presence of the depressions and/or holes is advantageous in that the wound exudate can penetrate particularly well at these points, as a result of which the absorption time can be reduced in a targeted manner.

In a particularly preferred embodiment of the invention, the foam layer is only partially covered by the adhesive layer. In the case of partial coverage, the adhesive layer can be present in the form of a regular or irregular pattern, for example as a lattice, hole, dot, dash, line, polygon, for example diamond or honeycomb, circle, cross, spot, and/or island pattern.

In a preferred embodiment, the adhesive layer is present as a non-coherent pattern, for example in the form of an island-like pattern. The advantage of this embodiment is that the foam layer can freely swell toward the wound bed when wound exudate is absorbed, and exudate absorption can thus still be ensured.

Mesh patterns have also proven to be particularly suitable patterns. An advantage of mesh patterns is that they prevent undesired lateral propagation of the wound exudate and thus maceration of the wound edge.

The adhesive layer may contain different materials. Preferred are materials or material combinations that adhere to healthy skin but not in contact with the wound. The materials for the adhesive layer are therefore advantageously selected such that, in the case of moist wounds, adherence and ingrowth of newly formed tissue is prevented, no pain is caused during removal of the dressing, and/or the wound is prevented from tearing open again.

Materials or material combinations suitable for use in the adhesive layer are adhesive materials that, with respect to use as a dermal patch, have a sufficiently adhesive and sufficiently slip-resistant effect. Particularly preferred are materials which exhibit a sufficiently adherent and sufficiently slip-resistant effect at least for a period of time sufficient to attach a secondary bandage, for example a dressing. Particularly suitable are silicones, particularly silicone gels, silicone elastomers, and/or crosslinked polyorganosiloxanes modified with substituents, such as polyethylene glycol and/or polyurethane. Also suitable are polyurethanes, such as polyurethane gels or polyurethane elastomers. Also suitable are partially or fully cured hydrophilic or hydrophobic gels, for example hydrogels, in particular based on acrylate and/or monosaccharide, as well as mixtures and/or copolymers thereof, hydrocolloid masses, and/or salve-like mixtures of solid and liquid hydrocarbons, in particular petroleum jelly.

In a particularly preferred embodiment according to the invention, the adhesive layer contains silicones. According to the invention, a wide variety of silicones, in particular silicone gels, can be used, provided they have the desired adhesive properties.

Silicones are inorganic/organic polymers based on repeating Si—O units with organic side chains. Silicones can form networks via siloxane bridges and/or the organic side chains themselves can form networks via covalent bonds. The silicones used according to the invention must, as explained above, exhibit adhesive properties. The person skilled in the art knows how to select the silicones so that they exhibit the desired adhesive properties, for example by targeted adjustment of the degree of crosslinking and/or entanglement, as well as of the network structure and/or network density.

According to the invention, preferred silicones are polyorganosiloxanes, in particular polyorganosiloxanes of the general formula I,

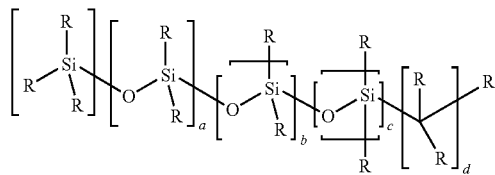

wherein the moieties R are independently of one another selected from the group consisting of hydrogen, C1-C8 alkyl, C6-C14 aryl, C4-C18 aryl alkyl, C4-C18 alkyl aryl, C2-C8 alkenyl, C1-C8 alkylidene, C1-C8 alkoxy (C1-C8) alkyl or poly(alkyleneoxy) alkyl groups. The aforementioned groups can be linear or branched and substituted or unsubstituted, where a, b, c, and d independently of one another represent a number between 0 and 10,000, preferably from 1 to 5,000.

The moieties R are preferably selected independently of one another from the group consisting of hydrogen, C1-C8 alkyl moieties, such as the methyl, ethyl, n-propyl, isopropyl, n-butyl, sec-butyl, amyl, hexyl moiety; C2-C8 alkenyl moieties, such as the vinyl, allyl, and butenyl moiety; C6-C14 aryl moieties, such as the phenyl moiety; C1-C8 alkylidene moieties, such as the methylene, ethylene, propylene and butylene moiety.

The moieties R are particularly preferably selected independently of one another from the group consisting of hydrogen, methyl, ethyl, propyl, phenyl, vinyl, ethylene.

In formula I, the following units

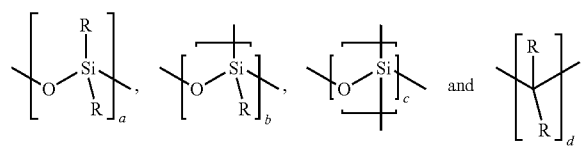

are repetitive units. As is known to the person skilled in the art, they can be present in the polymer in different sequences, that is to say, for example, in a blockwise, statistically distributed, and/or recurrent sequence.

The unit

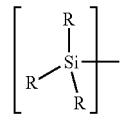

and the moieties R in formula I are end groups.

Suitable silicones according to the invention are preferably addition-crosslinking silicone compositions. These may be one-component silicone compositions and two- or multi-component silicone compositions, preferably two-component silicone compositions (components A and B). Room-temperature crosslinking two-component silicone compositions are very particularly preferably in this respect. The term "room-temperature crosslinking" is understood to mean crosslinking at temperatures from 15° C.

For producing the silicones starting from the two-component silicone compositions, a suitable catalyst, preferably a heavy metal and in particular a platinum catalyst, is preferably used. In particular liquid two-component systems from silicone precursor compounds in which one component contains the catalyst have proven suitable. The silicone precursor compounds may be mixed and placed on a substrate where they cure to form the silicone gel.

Component (A) particularly preferably contains vinyl-functional, substantially linear or slightly branched polydiorganosiloxanes with a viscosity of 10 to 100,000 mPa·s, preferably of 100 to 10,000 mPa·s, particularly preferably of 200 to 2,000 mPa·s, in each case at 25° C.

Component (B) particularly preferably contains Si—H-functional, substantially linear or slightly branched polydiorganosiloxanes with a viscosity of 10 to 100,000 mPa·s, preferably of 100 to 10,000 mPa·s, particularly preferably of 200 to 2,000 mPa·s, in each case at 25° C.

In addition, component A and/or B, preferably component A, contains the catalyst.

In a particularly preferred embodiment, the silicone is present in the form of a silicone gel. A silicone gel is understood according to the invention to be a silicone that has a polymer network suspended in a liquid sol phase. The silicone gel is preferably viscoelastic and/or has a penetration of 20 to 500 1/10 mm, more preferably from 50 to 300 1/10 mm (measured in accordance with DIN ISO 2137). An advantage of the use of silicone gels is that they simultaneously allow atraumatic removal and good adhesion on the skin.

Two-component silicone compositions suitable for the purposes according to the invention are known from the prior art and are described, for example, in EP 0251810 A1, EP 0300620 A1, and U.S. Pat. No. 4,921,704 A1. These systems substantially comprise a component A containing a vinyl-substituted polydiorganosiloxane, especially polydimethylsiloxane, and a platinum catalyst. Component B contains the polydiorganosiloxane having hydrogen atoms bonded directly to the silicon atom. Where applicable, the systems can contain further additives, such as fillers, therapeutically active substances such as silver ions, pigments, stabilizers, and/or inhibitors.

By mixing the two components, the metal-catalyzed addition reaction of the vinyl and Si—H groups, which leads to crosslinking and curing of the polydiorganosiloxanes, can be started. In this case, the silicone can arise in layer form and cure to form a crosslinked gel. In the process, the properties of the cured silicone gel can be influenced in different ways, for example by varying the ratio of components A and B, by varying the molecular weights and/or degree of branching of the polysiloxanes used, by varying the contents of the groups in components A and B responsible for crosslinking and their distribution on the polydiorganosiloxane precursor molecules (functionality) or by the concentration of the optionally added additive(s). Silicone gels can thus be produced which are pleasantly soft to touch, have high cohesion and at the same time significant adhesion to the skin.

Silicone gel precursor compositions are commercially available, for example, from Wacker under the product name Silpuran® and the type numbers 2110, 2112, 2120, or 2130, or from NuSil Technologies under the product designations MED-6342, MED-6345, or MED-6350 or from Dow Corning GmbH under the product designations MG 7-9800, MG 7-9850, or MG 7-9900.

The adhesive layer preferably contains the adhesive materials, for example the aforementioned materials, and in particular the silicones, in an amount of at least 20% by weight, for example from 20% by weight to 100% by weight, and more preferably from 50% by weight to 100% by weight, and in particular from 80% by weight to 100% by weight.

According to the invention, the dermal patch has a foam layer. The use of the foam layer as a wound dressing is advantageous in that it can absorb excess wound exudate and thus concomitantly can adjust an optimum climate for improving wound healing. By swelling when wound exudate is absorbed, the foam layer can also make filling of the wound bed possible. This is advantageous because it allows wound exudate to be absorbed over the entire wearing period.

According to the invention, the foam layer is characterized in that at least the side facing the adhesive layer has macropores which preferably adjoin the surface of the foam layer and whose cavities are spanned at least partially by a barrier layer formed from the foam layer. As already explained above, this special structure of the surface of the foam layer can be brought about in a simple manner by foaming a foam mixture in air. Alternatively, the foam mixture may be poured onto a support material, such as a casting paper. Without determining a mechanism, it is believed that, upon contact with the casting paper, the macropores arranged on the surface facing the casting paper are formed closed-celled.

The foam layer preferably has, and more preferably consists of, a polymer foam. Any polymer foam customary in modern wound treatment can be used. A polyurethane foam, a polyether foam, a polyurethane polyether copolymer foam, a polyvinyl acetate foam, a polyvinyl alcohol foam, a collagen foam, a chitosan foam, or mixtures of these foams can in particular be used as polymer foam. A polyurethane foam is particularly preferred. In a preferred embodiment, a hydrophilic polymer foam can be used as the polymer foam, the aforementioned polymers preferably being hydrophilic. Very particularly preferably, the polymer foam is a hydrophilic polyurethane foam. In the context of the present invention, the term "hydrophilic polymer foam" is to be understood to mean a polymer foam that can absorb and/or store liquids.

The hydrophilic polyurethane foam may contain a very wide variety of prepolymers and adjuvants.

The hydrophilic polyurethane foam may be produced by mixing an isocyanate-terminated polyether as a prepolymer having a functionality of more than two with a surfactant and water, and pouring the mixture onto a surface.

Figure 8:
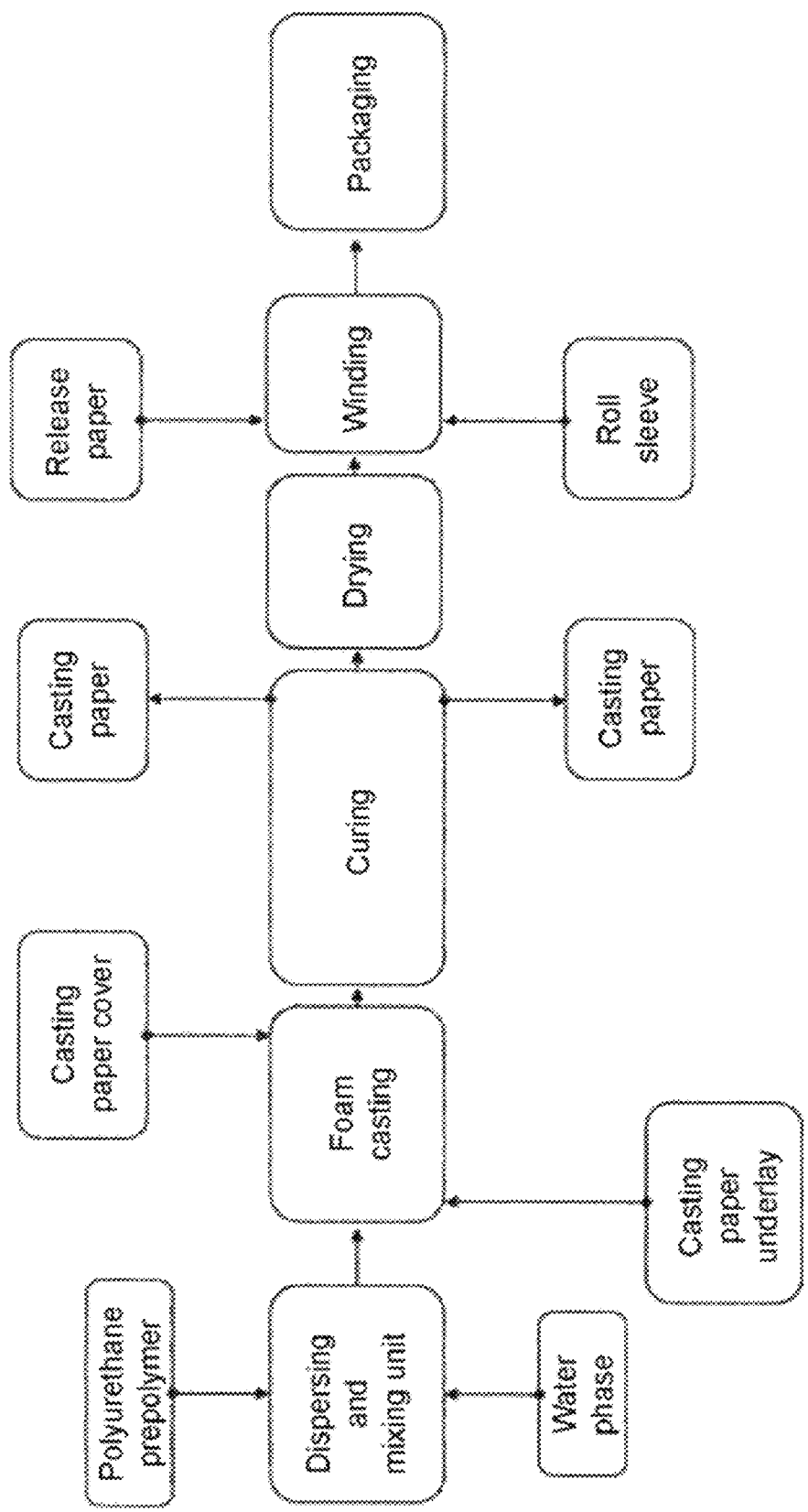
FIG. 8 depicts a sequence of a production process of a polyurethane foam layer in the casting method (according to the invention)

FIG. 8 schematically describes a preferred sequence of the production process of a polyurethane foam layer in the casting method ("cast to thickness").

The prepolymers can be prepared as reaction products from polyalkylene glycol ethers, ethoxylated glycerols, and/or polyalkylene glycol monoalkaryl ethers with aliphatic and/or aromatic diisocyanates, such as toluene-2,4-diisocyanate, methylene di(phenyl isocyanate), hexamethylene diisocyanate, and/or aliphatic and/or aromatic polyisocyanates.

The following adjuvants may be used: Detergents, particularly preferably non-ionic detergents and very particularly preferably detergents based on polyethylene glycol monolauryl ethers having an average molecular weight of about 350 to 1,100, polyethylene glycol monomethyl ethers having an average molecular weight between 500 and 5,000, and/or polyalkylene glycol ethers.

Other adjuvants may also be added, such as antioxidants, antimicrobial active ingredients such as silver, silver-containing substances, polyhexamethylene biguanide, iodine, chlorhexidine, honey, acetic acid, and/or potassium permanganate, and/or antibacterial substances based on quaternary ammonium salts.

In a further preferred embodiment of the invention, the foam layer has an average thickness of at least 0.5 mm, preferably 1 mm to 10 mm, and in particular 1 mm to 7 mm.

In a further preferred embodiment of the invention, the average density of the foam layer is at least from 50 kg/m$^3$, preferably from 70 kg/m$^3$ to 150 kg/m$^3$, and in particular from 90 kg/m$^3$ to 150 kg/m$^3$.

According to the invention, the dermal patch has a foam layer and an adhesive layer arranged thereon. In addition, the dermal patch can also contain further layers. For example, it is preferred for some applications when a liquid barrier layer is arranged on the side of the foam layer facing away from the adhesive layer in order to prevent unwanted leakage of liquid from the dermal patch. The most varied layers, for example polyurethane films, can be used as the liquid barrier layer.

It is likewise conceivable to use further, preferably absorbent layers and/or coatings, for example a (super)absorbent layer, such as a (super)absorbent nonwoven, and/or (super) absorbent particles. These further absorbent layers and/or coatings are preferably arranged on the side of the foam layer facing away from the adhesive layer and optionally between the foam layer and a liquid barrier layer.

A further object of the invention comprises a method for producing a dermal patch. This method comprises the following steps:

(A) Producing and/or providing a foam layer which at least on one side has macropores, the cavities of which are at least partially spanned by a barrier layer formed from the foam layer;

(B) Applying an adhesive material and/or precursor compounds thereof to the at least one side of the foam layer comprising the barrier layer;

(C) Optionally curing the adhesive material and/or precursor compounds thereof to form an adhesive layer.

A dermal patch described above may advantageously be produced using the method according to the invention.

In step (A), a foam layer is produced and/or provided which at least on one side has macropores, the cavities of which are spanned at least partially by a barrier layer formed from the foam layer. The foam layer can be produced in various ways, for example those described above. The advantageous nature of the foam layer can, as explained above, be achieved, for example, by foaming in air and/or by using a hydrophobic casting paper.

In step (B), an adhesive material and/or a precursor compound thereof is applied to at least one side of the foam layer. The adhesive materials and/or precursor compounds thereof particularly suitable according to the invention have already been mentioned above.

The adhesive material and/or precursor compounds thereof can be applied in a wide variety of ways. Spraying, roller application, in particular kiss-roll coating, and slot die application have proven to be particularly suitable since these methods are particularly well suited for applying coatings with a low weight per unit area without damaging the barrier layer. The application is preferably accomplished by contact-free or contactless application methods. The application by means of spraying has proven to be particularly suitable.

In the aforementioned methods, it has proven to be expedient to apply the adhesive material and/or precursor compounds thereof with a viscosity of less than 5,500 mPa·s, preferably from 1 mPa·s to 3,000 mPa·s, and more preferably from 100 mPa·s to 1,500 mPa·s.

If the application is to only result in partial covering by the adhesive layer, the application by a mask (mask application) has proven to be particularly suitable. In this case, the foam layer is expediently covered with a mask before the adhesive material and/or the precursor compounds thereof are applied, the mask containing openings in the desired patterns. After application of the adhesive material and/or precursor compounds thereof, the mask may be removed.

If precursor compounds of the adhesive material are used, they are preferably mixed before they are applied to the foam layer. In a further preferred form, the precursor compounds are first mixed on the foam layer.

Depending on the materials used, an adhesive layer can be formed directly by steps (A) and (B). In a preferred embodiment of the invention, after method steps (A) and (B), the adhesive material and/or precursor compounds thereof are cured to form the adhesive layer (C).

In a preferred embodiment of the invention, steps (A), (B), and optionally (C) are followed by a further method step (D) in which depressions and/or perforations are introduced into the adhesive layer and/or the foam layer. This can take place, for example, by locally removing parts of the adhesive layer and/or the foam layer. For example, a laser, in particular a $CO_2$ laser, can be used for this purpose.

The dermal patch can be used for a wide variety of medical and non-medical applications. In the non-medical area, applications are, for example, conceivable in which the moisture near the skin is to be regulated, i.e., as moisture-regulating dermal patch. In the medical field, the use for treating wounds is particularly preferred according to the invention.

As explained above, due to the barrier layer present, it is possible to achieve a small layer thickness of the adhesive layer with nevertheless a favorable adhesion property. An advantage of a thin adhesive layer is that any active substances contained in the foam layer can be present in the wound at a smaller distance from their site of action, and water vapor permeability can be improved.

As a result of the small layer thickness, low peeling forces can moreover be achieved, whereby the removal of the dermal patch can be made gentler to the skin.

In addition, the dermal patch when used as a wound dressing has the advantage, even in comparison to foams that are open-celled at the surface, that the barrier layer can prevent ingrowth of newly forming tissue. In this way, damage to the newly formed tissue can be avoided when changing the wound dressing.

The dermal patch according to the invention has an open-cell foam layer and can thereby exhibit good absorbency and absorption time. It is therefore outstandingly suitable for producing a moist wound climate and consequently for moist wound treatment, in particular of chronic wounds.

In addition, other medical uses are also conceivable, for example for preventing pressure ulcers (decubitus ulcer prevention).

Measuring Methods

For the purposes of the present invention, the following measuring methods were used:

Basically, in all measuring methods in which averages are formed, the person skilled in the art selects the number of values to be averaged depending on their spread. The higher the found deviations are, the more values the person skilled in the art includes in the determination.

Optical evaluation of SEM images: Scanning electron microscopy examinations are carried out at an acceleration voltage of 20 kV. In order to avoid charging effects and resulting measurement errors, the samples are sputtered with gold prior to the SEM examination. This takes place at an argon gas pressure of 0.1 hPa (0.1 mbar) with a sputtering current of 30 mA at a distance of 10 cm. The sputtering time is 300 seconds.

Measurement of the planarity of the barrier layer: The planarity is determined by optical evaluation of SEM measurements. A fictitious reference surface is generated by applying a paper that is coated on both sides with polyethylene and has a weight per unit area of 120 $g/m^2$ to the adhesive layer. In order to determine the planarity, the distance between the underside of the paper and the highest foam-containing location is determined at at least 10 measuring points evenly distributed over a range of at least 2 mm. The truncated average and the standard deviation are determined. The truncated average is formed by excluding the 10% highest and 10% lowest values. The determined standard deviation of the truncated sample corresponds to the planarity.

Thickness of the barrier layer: The thickness is determined by optical evaluation of SEM measurements of a cross section of the barrier layer. The regions where macropores are present are used in this case. The average of at least 5 values is formed.

Thickness of the adhesive layer: A fictitious reference surface is generated by applying a paper that is coated on both sides with polyethylene and has a weight per unit area of 120 g/m² to the adhesive layer. The thickness is determined at the respective measuring point as the distance between the underside of the paper and the lowest, adhesive-containing location. The evaluation is carried out in a cross section by means of SEM. If it increases the contrast between the adhesive and the foam layer, a backscatter detector is used. The thickness is measured at at least 10 locations evenly distributed over a range of at least 2 mm and the average is determined. In order to prevent falsification by subsequent penetration of adhesive into the foam layer when forming the cross-sectional area, the cut is made perpendicularly from the side of the foam layer facing away from the adhesive.

Applied quantity of the adhesive layer: The applied quantity of the adhesive layer is determined by weighing before and after coating and by forming the difference. Preferably, the size of the sample is at least 100 cm².

Degree of coverage of the adhesive layer: The degree of coverage is determined by optical evaluation of SEM measurements, preferably recorded in a plan view on the adhesive layer. If it increases the contrast between the adhesive and the foam layer, a backscatter detector is used. Preferably, the size of the sample is at least 4 cm².

Determination of adhesion: Adhesion is determined on the coated, 25 mm wide samples by tensile tests. For this purpose, the median of the peak peel resistances, with a peak definition of 0.5 mN, against a cleaned steel substrate is determined in accordance with DIN EN 1939:2003. The peeling angle is 180°, and the peeling speed is 300 mm/min. The adhesion is specified in the unit N/2.5 cm.

Pore diameter of the pores in the foam layer: The pore diameter is determined by optical evaluation of SEM images by applying an outer circle. The pore diameter corresponds to the diameter of the outer circle. The average is formed by evaluating at least 10 pores.

Thickness of the foam layer: The thickness of the foam layer is measured by a thickness measuring device at at least 5 locations evenly distributed over the sample. In doing so, it must be ensured that the foam is not compromised by the measuring device.

Density of the foam layer: The density is determined by cutting out a sample, weighing it, and determining the thickness. The volume is then calculated by multiplying the thickness by the area of the sample; and finally, the weight is divided by the volume.

Absorbency: For absorption measurements, a test solution as described in BS EN 13726-1:2002 is used. A 25 cm² large sample is first weighed (W1), then immersed in the test solution and left there for at least one minute. Afterwards, the sample is carefully grasped at one corner without squeezing the foam layer and let drip for 10 minutes. The weight is then determined again (W2). Now the absorbency is calculated by dividing the difference in the magnitude of W1 and W2 by the initial weight W1.

Optical differentiation between spanned and non-spanned macropores: The surface of the foam layer facing the adhesive layer is examined by means of SEM. Macropores having a perforation (see perforation of the barrier layer) are to be regarded as not spanned by the barrier layer.

Perforation of the barrier layer: A perforation is only considered as such if its diameter is greater than 25 µm. The diameter is determined by applying an outer circle. The resulting outer circle corresponds to the diameter of the perforation.

Determination of the proportion of macropores spanned by the barrier layer: In order to determine the number of macropores spanned by the barrier layer, the surface is analyzed in a plan view using SEM. Advantageously, an area of at least 25 mm² is examined. Only partially visible pores, for example in the edge regions, are not taken into consideration. If a plurality of layers of pores can be seen in the plan view, only the topmost layer is taken into consideration. The differentiation between spanned and non-spanned macropores is performed as described above. The number of spanned macropores is divided by the total number of macropores considered.

Determination of the percent area of the barrier layer to the 2D surface area of the foam layer: In order to determine the percent area of the barrier layer to the 2D surface area of the foam layer, the surface is analyzed in a plan view using SEM. Advantageously, an area of at least 25 mm² (corresponding here to the total 2D surface area) is examined. Only partially visible pores, for example in the edge regions, are taken into consideration. The area of the perforations (>25 µm) is graphically determined and summed. The difference in the magnitude of the sum from the total 2D surface area is divided by the total 2D surface area.

Determination of the penetration of the silicone gel: The penetration of the silicone gel is measured in accordance with DIN ISO 2137 by the depth of the sinking of a cone (weight 62.5 g) after 60 seconds.

EXAMPLES

The invention is explained in more detail below with reference to several examples.

Example 1: Production of a Foam Layer with Barrier Layer

A water phase is prepared for foam production by dissolving/dispersing the surfactant Pluronic F87 at a concentration of 0.5% by weight. At the same time, a Teflon mold with a sufficient depth around a foam of 7 mm thickness is lined with casting paper. The prepolymer Hypol 2001 is added to the water phase with a concentration of 40% by weight and mixed at room temperature with a dispersion disk (1,600 rpm). The resulting mixture is immediately poured into the casting mold. It is foamed in air and cured for 10 minutes. Thereafter, the casting paper is removed, and drying takes place at a temperature of 150° C. for 3 hours.

Example 2: Preparation of a Silicone Adhesive and Application of the Adhesive to Foam Layers with Different Proportion of Macropores Spanned by the Barrier Layer Three different 5 mm thick samples of foam layers with different proportions (specified in %) of macropores spanned by the barrier layer are provided.

Sample 1: Freudenberg 3112 top (79%)
Sample 2: Freudenberg 3112 underside (98%)
Sample 3: Essentra Medisponge® SuperSoft™ 60P (3%)

It is believed that the different proportion of macropores spanned by the barrier layer in type Freudenberg 3112 arises as a result of the influence of gravity in the production process.

A silicone adhesive precursor composition is freshly prepared by mixing the components Silpuran 2130 A and B in the stoichiometric ratio in a tumble mixer at 2,300 rpm for 1 minute. The liquid silicone adhesive precursor composition is sprayed onto the aforementioned samples using a hand Perfekt 4 spray nozzle of the gravity feed cup design by Krautzberger with a 0.8 mm spray head at 0.25 MPa (2.5 bar) air pressure. After curing the silicone adhesive precursor composition for 5 min at 100° C., the adhesion is determined in accordance with DIN EN 1939:2003.

For sample 1 with a 98% proportion of macropores spanned by the barrier layer, an adhesion results of $F$=0.13 N/2.5 cm in the case of a full-area silicone adhesive layer of 30 g/m$^2$, and of $F$=0.08 N/2.5 cm in the case of a silicone adhesive layer of 10 g/m$^2$.

For sample 2 with a 79% proportion of macropores spanned by the barrier layer, an adhesion of only $F$=0.06 N/2.5 cm in the case of a full-area silicone adhesive layer of 25 g/m$^2$ results.

For sample 3 with a 3% proportion of macropores spanned by the barrier layer, the adhesion cannot be measured in the case of a full-area silicone adhesive layer of 30 g/m$^2$.

It is shown that higher adhesion can be achieved with a higher proportion of macropores spanned by the barrier layer, even if the applied adhesive quantity is lower.

Example 3: Partial Application of the Adhesive on the Surface

A silicone adhesive precursor composition prepared as described in example 2 is sprayed using a Perfekt 4 hand spray nozzle of the gravity feed cup design by Krautzberger with a 0.8 mm spray head at 0.25 MPa (2.5 bar) air pressure onto sample 1 of example 2. In order to produce a regular pattern of adhesive dots on the foam, masks with normally offset (hexagonal) round perforations are used, which have
1) a 4.7 mm hole diameter and a separation of 6.5 mm, and
2) a 2.6 mm hole diameter and a separation of 3.8 mm.

With both masks, an average peel resistance of $F$=0.08 N/2.5 cm with a silicone adhesive layer of 10 g/m$^2$ on the polyurethane foam is determined.

FIG. 1 shows an SEM image of a foam layer of a dermal patch according to the invention in a plan view. The macropores spanned by the barrier layer and a perforation of the barrier layer can be seen clearly.

Figure 2:
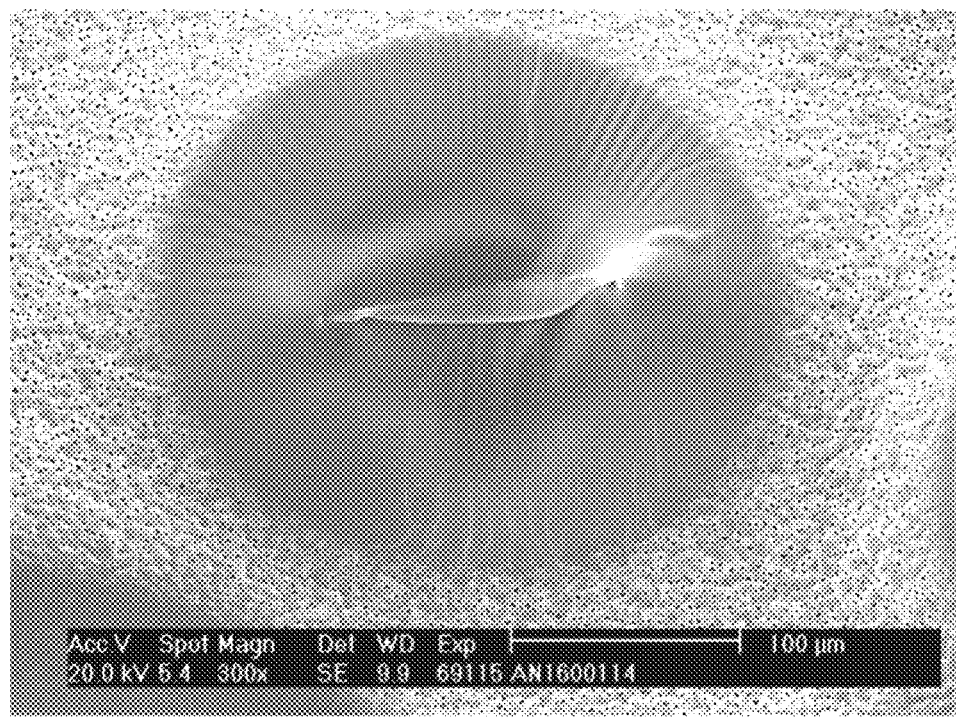
FIG. 2 SEM image of the barrier layer in a plan view (according to the invention)

FIG. 2 shows an SEM image of the barrier layer of a dermal patch according to the invention in a plan view. A macropore spanned by the barrier layer and many micropores can be seen in the image.

Figure 3:
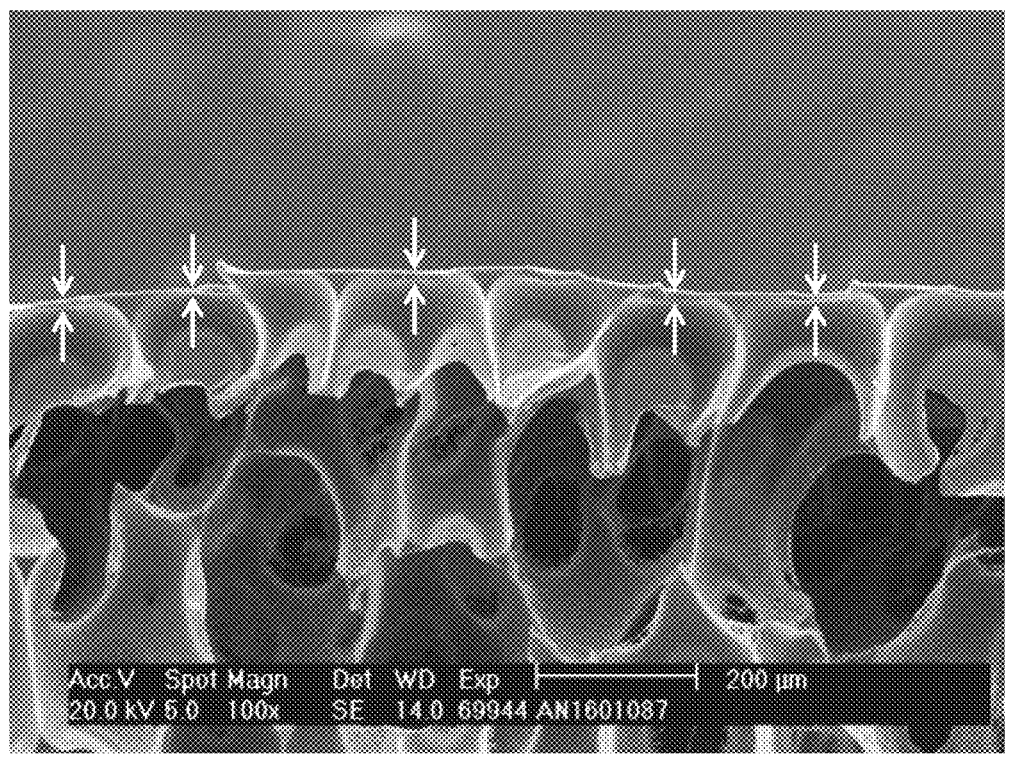
FIG. 3 SEM image of the foam layer in a cross section (according to the invention)

FIG. 3 shows an SEM image of the foam layer of a dermal patch according to the invention in a cross section. White arrows indicate various locations for determining the thickness of the barrier layer.

Figure 4:
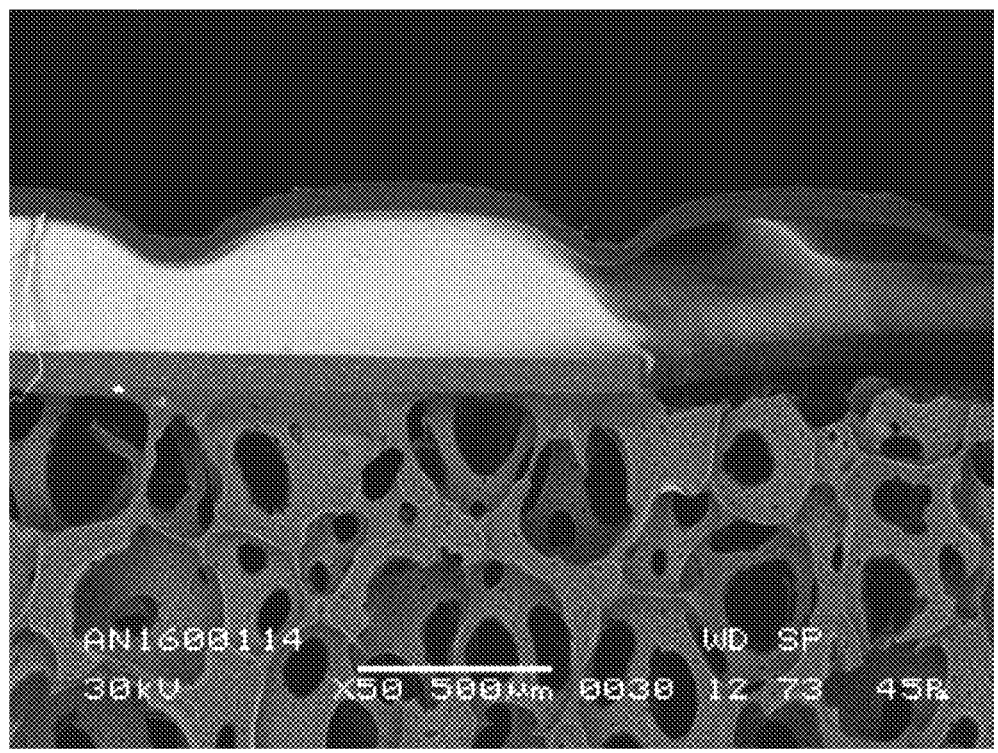
FIG. 4 SEM image of a foam layer with film as the barrier layer with an adhesive layer in a cross section (not according to the invention)

FIG. 4 shows an SEM image of a foam layer with film as barrier layer with an adhesive layer in a cross section (not according to the invention). The adhesive layer was applied here by means of a transfer coating method.

Figure 5:
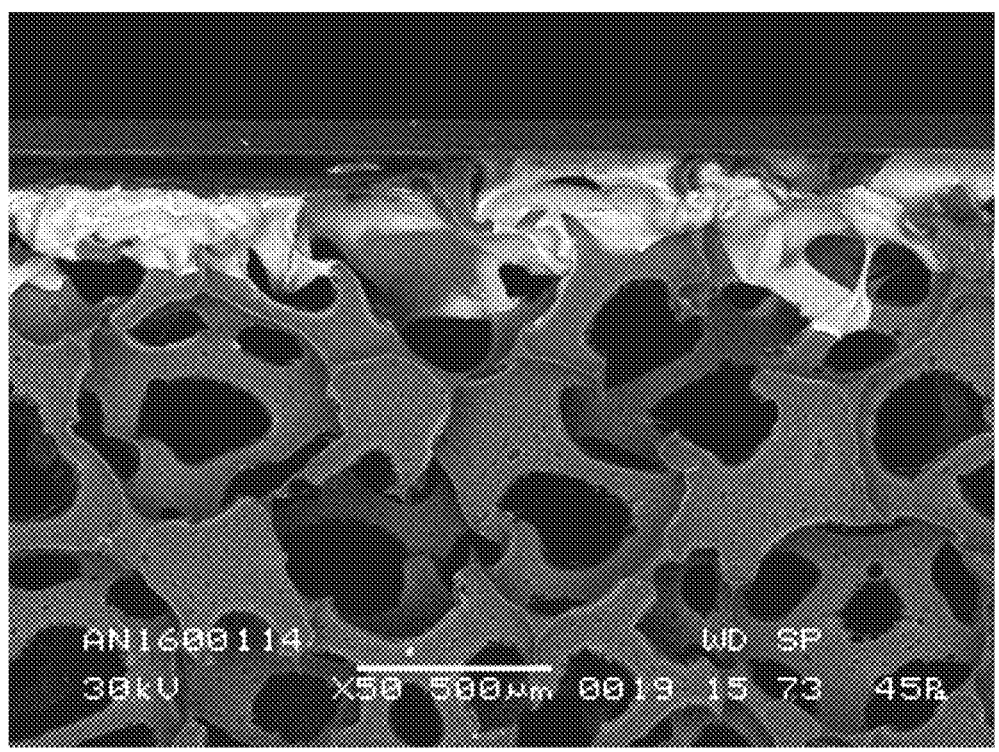
FIG. 5 SEM image of a foam layer without a barrier layer with an adhesive layer in a cross section (not according to the invention)

FIG. 5 shows an SEM image of a foam layer without a barrier layer with an adhesive layer in a cross section (not according to the invention). It can be seen that the adhesive layer has penetrated into the foam layer to a considerable extent.

Figure 6:
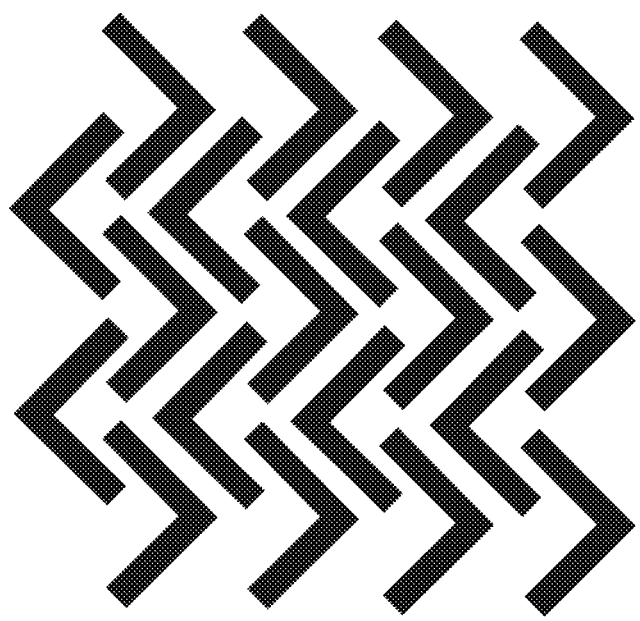
FIG. 6 Mesh pattern A

FIG. 6 shows a mesh pattern that can prevent lateral propagation of wound exudate.

Figure 7:
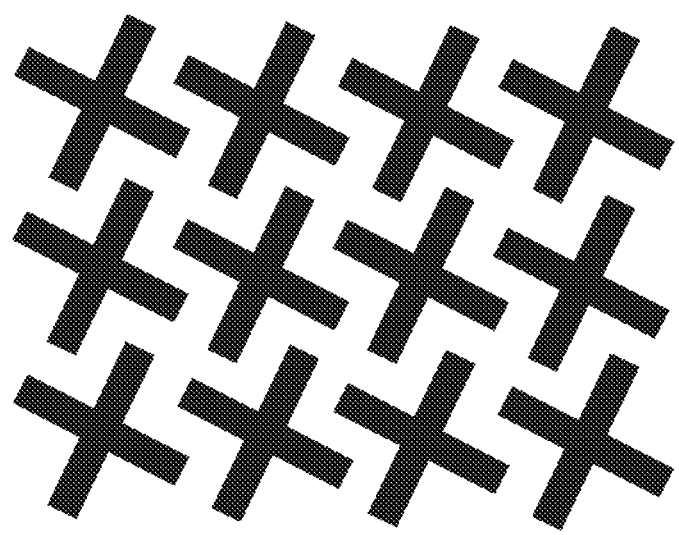
FIG. 7 Mesh pattern B

FIG. 7 shows another mesh pattern that can prevent lateral propagation of wound exudate.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A dermal patch, comprising:
   an open-cell foam layer having macropores with cavities;
   a barrier layer formed from the foam layer on one side of the foam layer and at least partially comprising a surface of the foam layer, the barrier layer at least partially spanning the cavities, wherein the barrier layer and the foam layer are integrally formed as a single structure, and wherein the barrier layer has a thickness of 0.3 µm to 20 µm; and
   an adhesive layer disposed on the barrier layer and configured for contact with skin.

2. The dermal patch according to claim 1, wherein the adhesive layer contains silicones.

3. The dermal patch according to claim 2, wherein the silicones comprise silicone gels, silicone elastomers, and/or crosslinked polyorganosiloxanes modified with substituents.

4. The dermal patch according to claim 3, wherein the substituents comprise polyethylene glycol and/or polyurethane.

5. The dermal patch according to claim 1, wherein the barrier layer has micropores.

6. The dermal patch according to claim 5, wherein the micropores have a pore diameter of 25 µm or less.

7. The dermal patch according to claim 1, wherein the foam layer comprises a hydrophilic polymer foam.

8. The dermal patch according to claim 7, wherein the hydrophilic polymer foam comprises a polyurethane foam.

9. The dermal patch according to claim 1, the dermal patch having an absorbency of at least 5 g/g.

10. The dermal patch according to claim 1, wherein a surface proportion of the barrier layer to a surface of the foam layer is at least 20%.

11. The dermal patch according to claim 1, wherein the barrier layer is planar.

12. The dermal patch according to claim 1, wherein the adhesive layer has a thickness of less than 200 µm and/or is present in an applied quantity of less than 200 g/m².

13. The dermal patch according to claim 1, wherein the adhesive layer is arranged directly on a surface of the foam layer.

14. The dermal patch according to claim 1, wherein the dermal patch has peak peel resistances against a steel substrate of more than 0.05 N/2.5 cm, even with applied quantities of adhesive of less than 200 g/m².

15. The dermal patch according to claim 1, wherein the adhesive layer only partially covers the foam layer, and/or a surface of the foam layer is formed only partially by the barrier layer.

16. The dermal patch according to claim 1, wherein the adhesive layer and/or barrier layer comprises a non-coherent and/or mesh pattern.

17. A dermal patch, comprising:
    an open-cell foam layer having macropores with cavities;
    a barrier layer formed from the foam layer on one side of the foam layer and at least partially comprising a surface of the foam layer, the barrier layer at least partially spanning the cavities and having a thickness of 0.3 µm to 20 µm; and
    an adhesive layer disposed on the barrier layer and configured for contact with skin,
    wherein the barrier layer is configured to partially prevent penetration of adhesive from the adhesive layer into the foam layer.

18. A dermal patch, comprising:
    an open-cell foam layer having macropores with cavities;
    a barrier layer formed from the foam layer on one side of the foam layer and at least partially comprising a surface of the foam layer, the barrier layer at least partially spanning the cavities, wherein the barrier layer is configured to increase permeability of wound exudate, sweat, or water vapor, and wherein the barrier layer has a thickness of 0.3 µm to 20 µm; and
    an adhesive layer disposed on the barrier layer and configured for contact with skin.

* * * * *